United States Patent [19]

Austin

[11] Patent Number: 4,962,123
[45] Date of Patent: Oct. 9, 1990

[54] THIOCYANATO-BUTENES AS INHIBITORS OF MICROORGANISM GROWTH

[75] Inventor: Peter W. Austin, Bury, England

[73] Assignee: Imperial Chemical Industries PLC, London, England

[21] Appl. No.: 237,748

[22] Filed: Aug. 29, 1988

[30] Foreign Application Priority Data

Sep. 23, 1987 [GB] United Kingdom ............... 8722358

[51] Int. Cl.$^5$ ..................... C07C 33/00; A01N 47/40
[52] U.S. Cl. ...................................... 514/514; 558/15
[58] Field of Search .......................... 558/15; 514/514

[56] References Cited

U.S. PATENT DOCUMENTS 4,087,451  5/1978  Merianos .............................. 558/15
4,545,994  10/1985  Schmitt et al. ....................... 558/15

Primary Examiner—Mary C. Lee
Assistant Examiner—Robert C. Whittenbaugh
Attorney, Agent, or Firm—William E. Dickheiser

[57] ABSTRACT

A halogenated ethylene compound of the formula:

$$X\ CR_1R_2C(Y_1)=C(Y_2)CR_1R_2\ SCN$$

where $R_1$ and $R_2$ are hydrogen, optionally substituted alkyl or together form a cyclohexyl group; X is bromine, chlorine or iodine and $Y_1$ and $Y_2$ are chlorine, bromine or iodine. A compound of this type is 2,3-dibromo-1-chloro-4-thiocyanato-2-butene. The compound has good anti-fungal and anti-bacterial properties. The compound can be used as an industrial biocide.

12 Claims, No Drawings

THIOCYANATO-BUTENES AS INHIBITORS OF MICROORGANISM GROWTH

The present invention relates to a class of compounds which are useful as industrial biocides, the production of such compounds and the use thereof.

More particularly this invention relates to a class of substituted ethylene thiocyanate compounds, which have antimicrobial properties, particularly antibacterial and/or antifungal properties, and which are useful as industrial biocides. Industrial biocides are useful to prevent industrial spoilage, in particular that caused by bacteria and fungi. Thus, such materials can be used in such applications as the preservation of paints, lattices, adhesives, leather, wood, metal working fluids and cooling water.

U.S. Pat. No. 4,087,451 discloses 2,3-dihalo-1,4-dithiocyano-2-butene and certain homologues thereof. Compounds of this type are stated to have antimicrobial properties and also fire retardant properties. However, no data is provided demonstrating either the antimicrobial or the fire retardant properties of these compounds. It has now been found that certain 2,3-dihalo-1,4-substituted-2-butene compounds have superior antimicrobial properties compared to compounds such as 2,3-dibromo-1,4-dithiocyano-2-butene. Furthermore, certain compounds are surprisingly active against both bacteria and fungi.

According to the present invention there is provided a compound of the general formula:

$$X\ CR_1R_2C(Y_1)\!=\!C(Y_2)CR_1R_2\ SCN$$

where
$R_1$ and $R_2$, which may be the same or different are hydrogen, a hydrocarbyl group, or a substituted hydrocarbyl group or $R_1$ and $R_2$, together with a carbon atom to which they are attached, form a ring structure;
X is bromine, chlorine or iodine; and
$Y_1$ and $Y_2$, which may be the same or different, are chlorine, bromine or iodine.

If $R_1$ and $R_2$ form a ring structure, this will typically be a cycloalkyl ring for example a cyclohexyl ring. $R_1$ and $R_2$ may be a hydrocarbyl or substituted hydrocarbyl group, such as an alkyl, cycloalkyl, aralkyl, alkaryl or aryl group, especially an alkyl group. If $R_1$ and/or $R_2$ are hydrocarbyl, typically the group contains no more than 20 carbon atoms, for example not more than 10 carbon atoms, particularly a lower alkyl group, that is an alkyl group containing 1 to 4 carbon atoms. The substituents, if present, can be, inter alia, hydrocarbyloxy groups, ester (that is acyloxy) groups, halogen atoms or nitrile groups and these groups may be further substituted. If $R_1$ and/or $R_2$ is substituted with halogen atoms, the group can contain more than one halogen atom, for example as in a trifluoromethyl group.

Preferred compounds are those in which at least one of the groups $R_1$ and $R_2$ is hydrogen and especially those in which both of $R_1$ and $R_2$ are hydrogen.

X is preferably chlorine or bromine. $Y_1$ and $Y_2$ are conveniently the same, for example $Y_1$ and $Y_2$ are both bromine.

The compounds can be obtained as the cis- or trans-isomers or as a mixture of such isomers. A compound consisting predominantly of the trans-isomer has been found to have useful antimicrobial properties.

Compounds in accordance with the present invention include
2,3-dibromo-1-chloro-4-thiocyanato-2-butene;
1,2,3-tribromo-4-thiocyanato-2-butene;
1-bromo-2,3-diiodo-4-thiocyanato-2-butene;
1-chloro-2,3-diiodo-4-thiocyanato-2-butene;
1,2,3-trichloro-4-thiocyanato-2-butene; and
1-bromo-2,3-dichloro-4-thiocyanato-2-butene.

All of the foregoing compounds show antifungal properties when tested against a range of different fungi. The compounds also show some antibacterial activity and compounds in accordance with the present invention which show a useful combination of antifungal and antibacterial properties include
2,3-dibromo-1-chloro-4-thiocyanato-2-butene;
1,2,3-tribromo-4-thiocyanato-2-butene;
1-bromo-2,3-diiodo-4-thiocyanato-2-butene; and
1-chloro-2,3-diiodo-4-thiocyanato-2-butene.

The compounds of the present invention are conveniently prepared by the reaction of a thiocyanate compound with a halogen containing precursor of the desired compound.

More specifically, a compound of the formula:

$$X\ CR_1R_2C(Y_1)\!=\!C(Y_2)CR_1R_2\ Z$$

is reacted with an alkali ate or ammonium thiocyanate
where
$R_1$, $R_2$, X, $Y_1$ and $Y_2$ are as defined; and
Z is a chlorine, bromine or iodine and is the same as or different from X.

If Z is different from X, Z is preferably a halogen atom which is more readily displaced by a thiocyanato group than the atom X. Thus, Z can be bromine or iodine when X is chlorine or iodine when X is bromine.

The thiocyanate compound and the compound $$X\ CR_1R_2C(Y_1)\!=\!C(Y_2)CR_1R_2\ Z$$

are conveniently reacted together in essentially equimolar proportions. If Z is different from X, the atom Z is more readily replaced and the reaction product is predominantly, or solely, the desired monothiocyanato compound. If X and Z are the same halogen, for example X and Z are both chlorine, some reaction may occur to give the dithiocyanato compound. Any dithiocyanato compound obtained, which is not desired, is separated from the desired monothiocyanato compound using any suitable technique. Typically the reaction is effected under conditions under which the dithiocyanato compound is essentially insoluble in the reaction solvent used, is precipitated from the reaction mixture and can be separated by filtration.

The reaction is preferably effected at a relatively low temperature, for example, not more than 80° C., such as ambient temperature (20°–25° C.) or lower, for example 15° C.

The reaction may be effected in any suitable solvent such as, for example, a lower alkanol, an aqueous lower alkanol, a ketone such as acetone, N,N-dimethylformamide, N-methylpyrrolidone, glyme, diglyme and cellosolve.

The desired butene-2 derivative can be isolated and purified using any suitable technique. Thus, the butene-2 derivative may be recrystallised from a suitable solvent such as, for example, a low boiling petroleum ether fraction. Alternatively, the butene-2 derivative may be purified by a chromatographic technique, for example by flash chromatography.

Compounds of the formula $$X\ CR_1R_2C(Y_1)=C(Y_2)CR_1R_2\ Z$$

from which the compounds of the present invention can be prepared, may themselves be obtained from 2-butyne-1,4-diol by halogenation to form a 2,3-dihalo-2-butene-1,4-diol followed by a further halogenation step, the process being generally as described in U.S. Pat. No. 4,087,451.

The butene-2 derivatives of the present invention have antimicrobial properties and, in particular, a number of the butene-2 derivatives show considerable activity against bacteria, fungi or both.

Thus, as a further aspect of the present invention there is provided a biocide composition which contains at least one compound of the formula:

$$X\ CR_1R_2C(Y_1)=C(Y_2)CR_1R_2\ SCN$$

where $R_1$, $R_2$, $X$, $Y_1$ and $Y_2$ are all as hereinbefore defined.

The compositions of the present invention provide good wet state preservation making the compositions advantageous for use, for example, as a cutting fluid preservative and also in cooling water applications. Wood and leather preservations is another advantageous field of application of the compositions. The compositions of the present invention can also be incorporated into paint as paint film fungicide.

The butene-2 derivatives which are present in a biocide composition in accordance with the present invention are soluble in many polar solvents, although the solubility is dependent on the nature of the groups $R_1$, $R_2$, $X$, $Y_1$ and $Y_2$. However, many of the compounds are soluble in water, alcohols, ethers, ketones and other polar solvents or mixtures thereof.

The compositions of the present invention may consist only of the butene-2 derivative. However, typically the composition comprises the butene-2 derivative together with a solid or liquid diluent. In general the composition comprises the butene-2 derivative as a solution, suspension or emulsion in a suitable liquid medium such as water. The composition may comprise a suspension or emulsion of the butene-2 derivative, or of a solution of the butene-2 derivative in a liquid medium in which the butene-2 derivative, and any solvent therefor which is present, is insoluble.

The composition may be incorporated into the medium to be protected using any suitable mixing technique. The composition is incorporated into the medium to be protected in an amount which is preferably sufficient to provide from 0.0001 to 5% by weight of the butane-2 derivative relative to the total composition. If the composition is being used to preserve a solid substrate such as leather or wood, the composition may be applied directly to the substrate or may be incorporated into a coating composition such as a paint, varnish or lacquer which is then applied to the substrate. Alternatively, the solid material may be impregnated with the composition of the present invention.

The compositions of the present invention can be used for the treatment of various media to inhibit the growth of microorganisms.

Thus, as a further aspect of the present invention there is provided a method for inhibiting the growth of micro-organisms on, or in, a medium which comprises treating the medium with a butene-2 derivative as hereinbefore defined.

The butene-2 derivatives can be used in conditions in which micro-organisms grow and cause problems such as, for example, in aqueous environments including cooling water systems, paper mill liquors, metal working fluids, geological drilling lubricants, polymer emulsions, and emulsion paints. The butene-2 derivatives can also be used to impregnate solid materials such as wood or leather or can be coated onto the surfaces thereof directly or incorporated into a paint, varnish or lacquer. It will be appreciated that the butene-2 derivatives will not be equally effective in all environments but the suitability of a compound for use in a particular situation can be determined using standard procedures.

The butene-2 derivatives of the present invention have been found to be particularly effective as paint film fungicides and are also effective in controlling the growth of micro-organisms in cooling water.

Thus, as a particular aspect of the present invention there is provided a paint formulation which contains an effective amount of a butene-2 derivative in accordance with the present invention.

As a further aspect of the present invention there is provided a method of controlling the growth of micro-organisms in cooling water by adding to the water an effective amount of a butene-2 derivative in accordance with the present invention.

Further aspects of the present invention are described in the following illustrative examples. In the following tests and examples, all parts are by weight unless stated to the contrary.

In the following examples, the products obtained were subjected to microbiostatic evaluation and some products were also subjected to evaluation as paint film fungicides and for bactericidal activity in an aqueous medium. The microbiological testing was effected, under sterile conditions throughout, as follows:

In the microbiological testing, the products were tested for anti-microbial activity against bacteria and/or fungi. The bacteria used were one or more of *Escherichia coli*, *Staphylococcus aureus*, and *Pseudomonas aeruginosa*. The fungi used were one or more of *Aspergillus niger*, *Aureobasidum pullulans*, *Cladosporium sphaerospermum*, *Aspergillus versicolor*, and *Chaetomium globosum*.

These test organisms will be referred to hereafter as EC, SA, PA, AN, AP, CS, AV and CG respectively.

Microbiostatic Evaluation

The material to be tested was dissolved in a suitable solvent and the solution obtained diluted with a further quantity of the same solvent to give a desired product concentration.

To a suitable agar medium was added a quantity of the product solution to give a desired concentration of the product. The agar medium containing the product was poured into petri dish plates and allowed to set.

The test organisms were surface inoculated onto the test plates by means of a multi-point inoculator. Each test plate was inoculated with both bacteria and fungi. The plates were incubated for four days at 25° C.

At the end of the incubation period, the plates were assessed visually for growth of the micro-organisms. The concentration of the product which inhibited the growth of a particular micro-organism was recorded.

Evaluation as a Paint Film Fungicide

The compound to be tested was dissolved in N,N-dimethylformamide to give a 10% by weight solution of the active ingredient. The solution obtained was added to samples of an exterior acrylic emulsion paint (based on Revacryl 1A latex at pH 9) in glass bottles and mixed to give final active ingredient levels in the paint of 1.0, 0.3 and 0.1% w/v.

The bottles containing paint plus biocide composition were sealed and stored at 40° C. for three days.

Small wooden test pieces were prepared for each paint composition by priming and then brushing on two full even coats.

One set of the coated test pieces were stored at ambient temperature in the dark. A further set of coated test pieces was placed in a leaching device in which the test pieces were sprayed with water for one day and the test pieces were removed from the leaching device and dried. Yet a further set of coated test pieces was subjected to leaching for two days.

The coated test pieces were then transferred to a high humidity chamber. Each test piece was then spray inoculated with a mixed fungal spore suspension of *Alternaria alternata*, *Aureobasidium pullulans*, *Cladosporium herbarum*, *Phoma violacea*, and *Stemphylium dendriticum*.

Incubation was carried out at 25° C. for four weeks. After this period the paint films were examined for fungal growth by naked eye and by stereo optical microscope.

EXAMPLE 1

5.76 parts of 2,3-dibromo-1,4-dichloro-2-butene (obtainable from Riedel-de-Haen AG) and 58 parts of acetone were stirred at ambient temperature until a clear solution resulted. 1.52 parts of ammonium thiocyanate were added and the reaction mixture was stirred at ambient temperature for 18 hours. A precipitate was formed which was collected by filtration, washed with cold water, and recrystallised from acetic acid to yield 1.1 parts of 2,3-dibromo-1,4-dithiocyanato-2-butene of m.p. 180° C. (This corresponds to the compound of Example 5 of U.S. Pat. No. 4,087,451).

By analysis the composition was found to be C 21.3% wt; H 0.8% wt; N 7.7% wt; and S 18.6% wt. $C_6H_4Br_2N_2S_2$ requires C 22.0% wt; H 1.2% wt; N 8.5% wt; and S 19.5% wt. This material will hereafter be referred to as Compound A.

The mother liquors from the above were evaporated to dryness using a rotary evaporator at a bath temperature of 40° C. and water pump vacuum, and the residue was flash chromatographed. A 10% chloroform solution in 60°-80° petroleum ether eluted a small amount of starting material while 2.8 parts of 2,3-dibromo-1-chloro-4-thiocyanato-2-butene were eluted with 50% and 60% chloroform solution in 60°-80° petroleum ether. The material was obtained as a white solid, melting point 66° C., by evaporating to dryness and recrystallising from 80°-100° petroleum ether.

By analysis the composition was found to be C 19.9% wt; H 1.3% wt; N 4.6% wt; Cl 10.6% wt; Br 53.2% wt; and S 10.6% wt. $C_5H_4Br_2ClNS$ requires C 19.6% wt; H 1.3% wt; N 4.6% wt; Cl 11.6% wt; Br 52.4% wt; and S 10.5% wt. The infra-red spectrum (KBr disc) showed an absorption peak at 2160 cm$^{-1}$, characteristic of SCN.

This product will be referred to hereafter as Compound 1.

EXAMPLE 2

1,2,3,4-tetrabromo-2-butene was prepared from 2-butyne-1,4-diol by reaction with bromine (as generally described in Example 2 of U.S. Pat. No. 4,087,451), followed by bromination of the intermediate 2,3-dibromo-2-butene-1,4-diol with phosphorus tribromide.

The procedure of Example 1 was repeated using 5.9 parts 1,2,3,4-tetrabromo-2-butene and 1.2 parts of ammonium thiocyanate to yield 1.4 parts of Compound A (as defined in Example 1) as an acetone insoluble precipitate. The mother liquors were processed as in Example 1 to give 2.3 parts of 1,2,3-tribromo-4-thiocyanato-2-butene as white crystalline compound, melting point 89°-91° C., after recrystallising from 80°-100° petroleum ether.

By analysis the product was found to be C 17.4% wt; H 1.1% wt; Br 69.3% wt; N 4.0% wt and S 9.0% wt. $C_5H_4Br_3NS$ requires C 17.1% wt; H 1.1% wt; Br 68.6% wt; N 4.0% wt and S 9.1% wt. This product will be referred to hereafter as Compound 2.

EXAMPLES 3 and 4

The compounds of Examples 1 and 2, together with compound A, were evaluated against a range of bacteria and fungi using the microbiostatic evaluation procedure described previously herein. Control for the test organisms was obtained at the levels set out in Table 1.

TABLE 1

| Organism | Compound under test (ppm) | | |
|---|---|---|---|
| | 1 | A | 2 |
| EC | 10 | 25 | 25 |
| SA | 2 | 25 | 2 |
| PA | 10 | 25 | 25 |
| AN | 5 | 500 | 5 |
| AP | 5 | 500 | 5 |
| CS | 5 | 500 | 5 |
| AV | 5 | 500 | 5 |
| CG | 5 | 500 | 5 |

EXAMPLE 5

1,4-dibromo-2,3-diiodo-2-butene was prepared from 2-butyne-1,4-diol by iodination as generally described in Example 3 of U.S. Pat. No. 4,087,451, and the intermediate 2,3-diiodo-2-butene-1,4-diol was brominated using phosphorus tribromide.

The procedure of Example 1 was repeated using 1.27 parts of 1,4-dibromo-2,3-diiodo-2-butene and 0.25 parts of ammonium thiocyanate. A precipitate was formed and this was collected by filtration, washing with cold water and recrystallisation from acetic acid to give 0.44 parts of 2,3-diiodo-1,4-dithiocyanato-2-butene of melting point 190° C. with decomposition.

By analysis the composition of this material was found to be C 17.3% wt; H 0.9% wt; I 60.2% wt; N 6.3% wt and S 14.9% wt. $C_6H_4I_2N_2S_2$ requires C 17.1% wt; H 0.9% wt; I 60.2% wt; N 6.4% wt and S 15.0% wt. This material will hereafter be referred to as Compound B.

The mother liquors were processed as in Example 1 with the exception that the product was recrystallised from 100°-120° petroleum ether. The product, 1-bromo-2,3-diiodo-4-thiocyanato-2-butene, was obtained as a white solid of melting point 84°-86° C.

By analysis the product was found to be C 13.8% wt; H 0.5% wt; Br 18.5% wt; I 56.3% wt; N 3.0% wt and S 7.3% wt. $C_5H_4BrI_2NS$ requires C 13.5% wt; H 0.9% wt; Br 18.0% wt; I 57.2% wt; N 3.2% wt and S 7.2% wt. This product will hereafter be referred to as Compound 3.

EXAMPLE 6

2,3-diiodo-2-butene-1,4-diol (prepared as described in Example 5) was chlorinated to give 1,4-dichloro-2,3-diiodo-2-butene using thionyl chloride, the general procedure being as described in Example 4 of U.S. Pat. No. 4,087,451.

The procedure of Example 1 was repeated using 3.8 parts of 1,4-dichloro-2,3-diiodo-2-butene to yield 1.34 parts of Compound B (as defined in Example 5) as an acetone insoluble precipitate. The mother liquids were processed as in Example 1 with the exception that the product was recrystallised from 60°-80° petroleum ether. 1.23 parts of 1-chloro-2,3-diiodo-4-thiocyanato-2-butene were obtained as a solid of melting point 76°-78° C.

By analysis the product was found to be C 15.4% wt; H 1.0% wt; Cl 8.9% wt; I 61.9% wt; N 3.4% wt and S 7.9% wt. $C_5H_4ClI_2NS$ requires C 15.0% wt; H 1.0% wt; Cl 8.9% wt; I 63.6% wt; N 3.5% wt and S 8.0% wt. This product will hereafter be referred to as Compound 4.

EXAMPLES 7 and 8

Compounds 3 and 4, together with Compound B, were evaluated against a range of bacteria and fungi using the microbiostatic evaluation procedure described previously herein. Control for the test organisms was obtained at the levels set out in Table 2.

TABLE 2

| Organism | Compound under test (ppm) | | |
|---|---|---|---|
| | 3 | B | 4 |
| EC | 50 | N | 10 |
| SA | 2 | 25 | 2 |
| PA | 50 | 500 | 50 |
| AN | 25 | 5 | 25 |
| AP | 5 | 5 | 5 |
| CS | 5 | 5 | 5 |
| AV | 5 | 5 | 5 |
| CG | 5 | 5 | 5 |

N Indicates that the compound showed no activity at the highest level (500 ppm) tested.

EXAMPLE 9

1,2,3,4-tetrachloro-2-butene was prepared from 2-butyne-1,4diol by reaction with chlorine (as generally described in Example 1 of U.S. Pat. No. 4,087,451) followed by chlorination of the intermediate compound (2.3-dichloro-2-butene-1,4-diol) using thionyl chloride as generally described in Example 4 of U.S. Pat. No. 4,087,451.

The procedure of Example 1 was repeated using 3.88 parts 1,2,3,4-tetrachloro-2-butene and 1.76 parts of ammonium thiocyanate. A precipitate was formed and this was collected by filtration, washing with cold water and recrystallisation from acetic acid to give 1.42 parts of 2,3-dichloro-1,4-dithiocyanato-2-butene of melting point 166°-169° C. This material will hereafter be referred to as Compound C.

The mother liquors were processed as in Example 1 to give 1.95 parts of 1,2,3-trichloro-4-thiocyanato-2-butene as a solid of melting point 60°-63° C.

By analysis the product was found to be C 27.5% wt; H 1.9% wt; Cl 50.0% wt; N 6.4% wt and S 14.5% wt. $C_5H_4Cl_3NS$ requires C 27.7% wt; H 1.8% wt; Cl 49.2% wt; N 5.5% wt and S 14.5% wt. This product will hereafter be referred to as Compound 5.

EXAMPLE 10

2,3-dichloro-2-butene-1,4-diol was brominated with phosphorus tribromide to give 1,4-dibromo-2,3-dichloro-2-butene.

The procedure of Example 1 was repeated using 4.24 parts of 1,4-dibromo-2,3-dichloro-2-butene and 1.32 parts of ammonium thiocyanate to yield 1.32 parts of Compound C (as defined in Example 9) as an acetone insoluble solid. The mother liquors were processed as in Example 1 to give 0.97 parts of 1-bromo-2,3-dichloro-4-thiocyanato-2-butene as a solid of melting point 64.5°-66.5° C.

By analysis the product was found to be C 23.3% wt; H 1.4% wt; Br 34.2% wt; Cl 25.7% wt; N 5.2% wt and S 12.2% wt. $C_5H_4BrCl_2NS$ requires C 23.0% wt; H 1.5% wt; Br 30.7% wt; Cl 27.2% wt; N 5.4% wt and S 12.3% wt. This product will hereafter be referred to as Compound 6.

EXAMPLES 11 and 12

Compounds 5 and 6, together with Compound C, were evaluated against a range of bacteria and fungi using the microbiostatic evaluation procedure described previously herein. Control for the test organisms was obtained at the levels set out in Table 3.

TABLE 3

| Organism | Compound under test (ppm) | | |
|---|---|---|---|
| | 5 | C | 6 |
| EC | 10 | N | 25 |
| SA | 10 | 25 | 10 |
| PA | 250 | N | 250 |
| AN | 5 | 25 | 25 |
| AP | 5 | 25 | 25 |
| CS | 5 | 5 | 25 |
| AV | 5 | 25 | 25 |
| CG | 5 | 5 | 25 |

N is as defined in Table 2

EXAMPLE 13

Compound 1 was evaluated as a paint film fungicide using the technique described previously herein. For comparative purposes paints containing a commercially available fungicide were evaluated under the same conditions. The results obtained are set out in Table 4.

TABLE 4

| Compound (a) | Concentration (b) (c) | | | | | |
|---|---|---|---|---|---|---|
| | 0.1 | | 0.3 | | 1.0 | |
| | UL | L | UL | L | UL | L |
| 1 | 0 | 3 | 0 | 2 | 0 | 0 |

TABLE 4-continued

| Compound | Concentration (b) (c) | | | | | |
|---|---|---|---|---|---|---|
| | 0.1 | | 0.3 | | 1.0 | |
| (a) | UL | L | UL | L | UL | L |
| X | 2 | 5 | 0 | 4 | 0 | 1 |

Notes to Table 4
(a) X is N-octylisothiazolone.
(b) Concentration is given as % w/v based on the paint.
UL means the test piece had not been leached.
L means the test piece had been leached.
(c) 0 indicates no surface growth.
1 indicates less than 1% fungal growth over surface.
2 indicates 1 to 10% fungal growth over surface.
3 indicates 10 to 30% fungal growth over surface.
4 indicates 30 to 70% fungal growth over surface.
5 indicates greater than 70% fungal growth over surface.

EXAMPLES 14 and 15

Compounds 1 and 3 were tested for bactericidal activity in an aqueous medium using the following procedure.

1 cm³ volume samples of a *Pseudomonas fluorescens* were transferred to 100 cm³ of World Health Organisation standard hard water (pH 8.5) in 250 cm³ flasks which contained various levels of added biocide.

The various mixtures were then incubated at 30° C. for a period of 4 hours in an orbital shaker, after which the number of surviving cells was determined by the decimal dilution method using nutrient agar.

The results obtained are set out in Table 5, together with the results obtained using Compound A (as defined in Example 1) and also, as a control, in the absence of any added biocide.

TABLE 5

| Compound | Conc. (ppm) (d) | Survivors (cells/cm³) after 4 hours |
|---|---|---|
| 1 | 200 | <10 |
| 1 | 50 | <10 |
| 1 | 12.5 | <10 |
| 1 | 3.125 | >3 × 10⁵ |
| 3 | 200 | <10 |
| 3 | 50 | <10 |
| 3 | 12.5 | 1.8 × 10³ |
| 3 | 3.125 | >3 × 10⁵ |
| A | 200 | >3 × 10⁵ |
| A | 50 | >3 × 10⁵ |
| A | 12.5 | >3 × 10⁵ |
| A | 3.125 | >3 × 10⁵ |
| — | NIL | 7.9 × 10⁷ |

Notes on Table 5
(d) The concentration is that of the active ingredient.

I claim:

1. A compound of the formula:

$$X CR_1R_2C(Y_1)=C(Y_2)CR_1R_2SCN$$

where
$R_1$ and $R_2$, which may be the same or different are hydrogen, a hydrocarbyl group, or a substituted hydrocarbyl group wherein the hydrocarbyl group contains no more than 20 carbon atoms and any substituents are selected from hydrocarboxyl groups, ester groups, halogen atoms or nitrile groups; or
$R_1$ and $R_2$, together with a carbon atom to which they are attached form a ring structure which contains not more than six carbon atoms;
X is bromine, chlorine or iodine; and
$Y_1$ and $Y_2$, which may be the same or different, are chlorine, bromine or iodine.

2. The compound of claim 1 wherein $R_2$ and/or $R_2$ is an alkyl group containing 1 to 20 carbon atoms.

3. The compound of claim 1 wherein $R_1$ and $R_2$ are both hydrogen atoms.

4. The compound of claim 1 wherein X is chlorine or bromine.

5. The compound of claim 1 wherein $Y_1$ and $Y_2$ are the same.

6. A butene-2 derivative which is
2,3-dibromo-1-chloro-4-thiocyanato-2-butene;
1,2,3-tribromo-4-thiocyanato-2-butene;
1,2,3-trichloro-4-thiocyanato-2-butene;
1-bromo-2,3-dichloro-4-thiocyanato-2-butene;
1-bromo-2,3-diiodo-4-thiocyanato-2-butene; or
1-chloro-2,3-diiodo-4-thiocyanato-2-butene.

7. A biocide composition which contains an effective amount of at least one of the compounds of claim 1.

8. The composition of claim 7 which is a solution, suspension or emulsion containing an effective amount of one of the compounds of claim 1.

9. A method of inhibiting the growth of micro-organisms on, or in, a medium which comprises treating the medium with an effective amount of at least one of the compounds of claim 1 or the composition of claim 7.

10. A medium which is susceptible to attack by micro-organisms and which contains an effective amount of from 0.0001 to 5% by weight of at least one of the compounds of claim 1.

11. A method of controlling the growth of micro-organisms in cooling water which comprises adding to the water an effective amount of at least one of the compounds of claim 1.

12. A process for the production of a compound as claimed in claim 1 which comprises reacting a compound of the formula:

$$XCR_1R_2C(Y_1)=C(Y_2)CR_2R_2Z$$

with an essentially equimolar proportion of an alkali metal thiocyanate or ammonium thiocyanate to produce a mixture of the monothiocyanate compound and the dithiocyanate compound and the monothiocyanate compound is separated from the dithiocyanate compound, wherein $R_1$, $R_2$, X, $Y_1$ and $Y_2$ are as defined in claim 1; and Z is a chlorine, bromine or iodine atom and is the same as, or different from X.

* * * * *